United States Patent
Pan et al.

(10) Patent No.: US 6,465,447 B1
(45) Date of Patent: Oct. 15, 2002

(54) SUBSTANCE HAVING STEROID-LIKE STRUCTURE, PROCESS FOR THE PRODUCTION THEREOF AND ANTITUMOR AGENTS CONTAINING THE SAME

(75) Inventors: Tair-Long Pan; Sigeru Goto; Chao-Long Chen, all of Kaohsiung (TW)

(73) Assignee: Hisamitsu Pharmaceuticals Co., Inc., Tosu (JP)

( * ) Notice: Subject to any disclaimer, the term of this patent is extended or adjusted under 35 U.S.C. 154(b) by 0 days.

(21) Appl. No.: 09/623,029

(22) PCT Filed: Feb. 25, 1999

(86) PCT No.: PCT/JP99/00889

§ 371 (c)(1),
(2), (4) Date: Aug. 25, 2000

(87) PCT Pub. No.: WO99/43698

PCT Pub. Date: Sep. 2, 1999

(30) Foreign Application Priority Data

Feb. 27, 1998 (JP) ............................. 10-064543

(51) Int. Cl.[7] ..................... A61K 31/575; A61K 9/20; A61K 9/14; A61K 35/84
(52) U.S. Cl. ..................... 514/179; 424/464; 424/451; 424/489
(58) Field of Search ................ 424/464, 451; 514/182, 179

(56) References Cited

FOREIGN PATENT DOCUMENTS

| JP | 1-296991 | 11/1989 |
|---|---|---|
| JP | 8-81386 | 3/1996 |
| JP | 9-235293 | 9/1997 |

OTHER PUBLICATIONS

Tsunoo et al., 'Non–Purinergic and Non–Adrengergic Effects of Cordyceps Sinensis (Tochu–Kaso) on Respiratory Tracts and Aortae', 16018, P2–191, p. 213.

Kiho et al., 'Polysaccharides in Fungi. XXXII. Hypoglycemic Activity and Chemical Properties of a Polysaccharide from the Cultural Mycelium of Cordyceps Sinensis', Biol. Pharm. Bull. 16(12) 1291–1293 (1993).

Kiho et al., 'Polysaccharides in Fungi XXXVI. Hypoglycemic Activity of Polysaccharide (CS–F30) from the Cultural Mycelium of Cordyceps sinensis and Its Effect on Glucose Metabolism in Mouse Liver', Biol. Pharm. Bull. 19)2) 294–296 (1996).

(List continued on next page.)

*Primary Examiner*—Edward J. Webman
*Assistant Examiner*—Helen Nguyen
(74) *Attorney, Agent, or Firm*—Fitch, Even, Tabin & Flannery (57) ABSTRACT

This invention provides a separation method by which a compound having an antitumor effect possessed by Tochukaso can be obtained in a pure state. Further, this invention reveals the chemical structure of the compound having such antitumor effect. Still further, the invention aims at providing an antitumor agent comprising said compound.

4 Claims, 10 Drawing Sheets

OTHER PUBLICATIONS

Yoshida et al., 'Potentiating Effect of an Extract of Cordyceps sinensis (Berk.) Sacc. on Cytostatic Activity of Mouse Effector Cells Against Tumor Cells', (J. Kanazawa Med. Univ.) 17:330–335, 1992.

Chatterjee et al., 'Cordyceps sinenis (Berkeley) Saccardo: Structure of Cordycepic Acid', Journal of the American Pharm. Assoc., vol. XLVI, No. 2, 114–118, (Feb. 1957).

Japanese Society For Immunology, vol. 18, 665 (1988).

Prog. Med. 12:1172–74 (1992) Japanese Journal of Bacteriiology 45, 763 (1990).

Kuo et al., 'Growth Inhibitors Against Tumor Cells in Cordyceps Sinensis Other Than Cordycepin and Polysaccharides', Cancer Investigation, vol. 12, No. 6, 1994, pp. 611–615.

Shiao et al., 'Natural Products of Cordyceps', Proceedings In the National Science Council Republic of China Part A, vol. 13, No. 6, 1989, pp. 382–387.

Kadota et al., 'Steroidal Components of I–Tiam–Hong and Cordyceps–Sinensis Separation and Identification By High–Performance Liquid Chromatography', Yakugaku Zasshi, vol. 106, No. 12, 1986, pp. 1092–1097.

SUBSTANCE HAVING STEROID-LIKE STRUCTURE, PROCESS FOR THE PRODUCTION THEREOF AND ANTITUMOR AGENTS CONTAINING THE SAME

This application is the national phase of international application PCT/JP99/00889 filed Feb. 25, 1999 which designated the U.S.

TECHNICAL FIELD

This invention relates to a method for separating an active fraction of Tochukaso (or *Cordyceps sinensis*) having antitumor activity and an active component contained therein, as well as to the chemical structure of the active component. Furthermore, the invention relates to an antitumor agent containing the active fraction or the active component.

BACKGROUND ART

Tochukaso is parasitic on insects or larvae thereof belonging to Lepidoptera (such as butterfly and moth) or Coleoptera to form sclerotium within their bodies; and it is a fruit body formed in summer on the body surfaces of the insects or larvae that are the hosts. Approximately 350 species of Tochukaso(s) are known in the world. It is a material that has traditionally been administered in oral form as a Chinese medicine since it has absolutely no toxicity to humans and exhibits a variety of effects. Today, it is listed in "The Pharmaceutical Sciences of Chinese Plants" and "The Encyclopedia of Chinese Medicines," which are the text books concerning Chinese medicines; in this country-Japan, it is also described in many Chinese medical references such as "Oriental Drugs, New Edition."

Pharmacological actions described in the various documents are believed to be such that they are effective for energy buildup, nourishment/robustness and circulatory diseases [The Japanese Journal of Pharmacology, 63, 213 (1995)], diabetes [Biol. Pharm. Bull., 16, 1291–1293 (1993); ibid., 19, 294–296 (1996)], hepatic disorders [Prog. Med., 12, 1172–1174 (1992)] and the like. Furthermore, recent pharmacological studies have demonstrated that the fungi of Tochukaso (*Cordyceps sinensis*) possess a wide variety of activities and pharmacological actions. The antitumor and immunopotentiation activities have also been reported in the Academic Records of the Japanese Society for Immunology, vol. 18, 665 (1988), Japanese Journal of Bacteriology, 45, 763 (1990), and J. Kanazawa Med. Univ. 17, 330–335 (1992).

However, there have been only a few cases where the active component of Tochukaso that had been completely purified was used for research and clinical purposes [J. Am. Pharm. Ass., 46, 114–118 (1957); Japanese Unexamined Patent Publication Hei 8-81386]. This posed the problem that large amounts of the Tochukaso bulk materials or tablets were required when the unpurified extracts were administered and also the problem in the uniformity or reliability of pharmacological action. Moreover, few studies have been done that are related to the classification and identification of active species from Tochukaso, as well as to the mechanism of manifestation of its pharmacological action. In Asian countries, including the People's Republic of China, where the greatest number of Tochukaso species has been found to live, medicinal herbs such as Pueravia Radix extract (Kakkon Tou) are taken brewing up. Thus, at present Tochukaso is being used following the customs and faiths of different regions. It has not yet reached the point where the pharmacological effect of Tochukaso can be maintained securely and stably.

Accordingly, in order to effectively and reliably utilize the pharmacological action of Tochukaso, particularly pharmacological effects such as antitumor activity and immunopotentiation activity, there is a strong need for the development of a method to separate an active component having the activity among the components of Tochukaso.

DISCLOSURE OF THE INVENTION

This invention takes note of an antitumor effect possessed by Tochukaso and aims at providing a separation method by which a compound having said effect can be obtained in a pure state. Further, an object of the invention is to provide a compound having such antitumor effect. Still further, an object of the invention is to provide an antitumor agent containing said compound.

BEST MODE FOR CARRYING OUT THE INVENTION

Figure 1A:
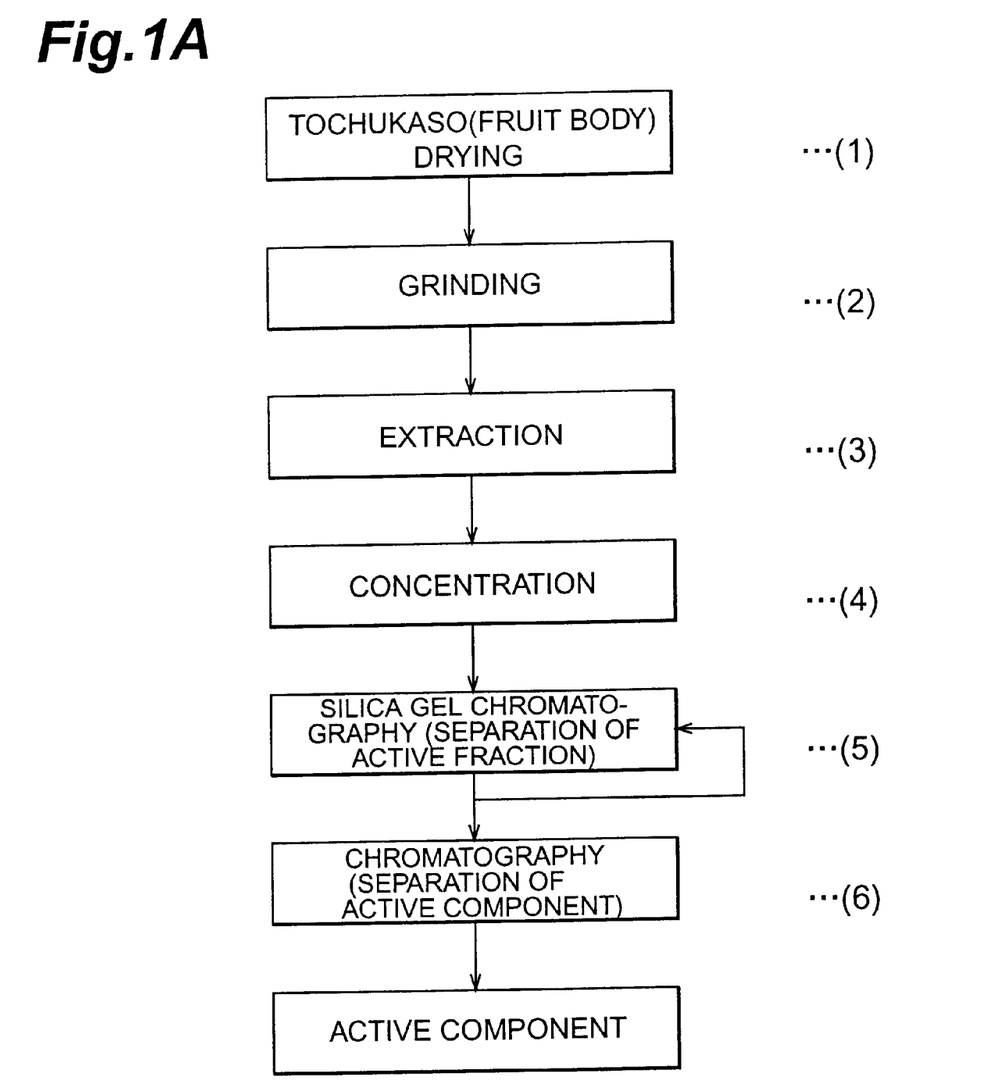
FIG. 1A is a general flow chart of the extraction of active fractions and active components from Tochukaso according to this invention.

A. This invention is characterized by a method for separating an active fraction and an active component with antitumor activity contained in Tochukaso, the method comprising:

drying a fruit body of Tochukaso;

grinding the dried fruit body to prepare a dried/ground sample;

extracting the sample with a water-miscible solvent to prepare an extracted solution;

concentrating the extracted solution to prepare a crude extract;

separating the crude extract by silica gel chromatography at least once to obtain an eluted fraction having a tumor cell proliferation inhibitory activity and to prepare the active fraction; and further purifying the active fraction by chromatography to separate the active component having the tumor cell proliferation inhibitory activity (FIG. 1A).

There is no particular limitation to the fruit body of Tochukaso that is a usable material for extraction in this invention. It may be a fruit body that is parasitic on an insect or larva thereof belonging to Lepidoptera (such as butterfly and moth) or Coleoptera, which is generally known, to form sclerotium within its body and that is formed in summer on the body surface of the host insect or larva. For Tochukaso that can most preferably be used in this invention, there may be mentioned *Cordyceps sinensis* that is parasitic on a larva of *Hepialus armoricanus* Ober belonging to Hepialus to form sclerotium within its body and that produces a fruit body in a rod form from the head in summer. Other than *Cordyceps sinensis*, known as Tochukaso that is an efficacious herbal drug are *Cordyceps sobolifera* B, *Cordyceps militaris* Link, and *Cordyceps nutans* Pat: these can also be preferably used in this invention. The method of this invention allows the extraction (separation) of these Tochukasos in any case where they produce an active component having antitumor activity as explained below. Also, following the method of the invention, the extraction is possible regardless whether it is from a fruit body or from an angiosperm body; however, extraction from the fruit body of *Cordyceps sinensis* is preferable in order to obtain high yields.

For a method for extracting and separating an active fraction or an active component that has antitumor activity, a method that is ordinarily used to extract substances from a plant may be employed without any particular limitations. The particularly preferred method for extraction and separation is shown below. In addition, there is no particular limitation to the method for determining the antitumor activity that is used to separate the active fraction or the active component having the activity; and it is easy to select and use ordinarily known methods. Specifically, a certain tumor cell may be selected and then the determination can be made based on its effect to inhibit proliferation of the cell.

As is generically shown in FIG. 1A, the method of this invention comprises the steps below.

(1) Step of drying a fruit body of Tochukaso which will serve as a raw material. This operation is done because polar substances are extracted together during the subsequent extraction and they quite often adversely affect the separation/purification treatment by chromatography if the water content of the raw Tochukaso material is very high. There is no particular limitation to the drying method, but a drying box of an appropriate size is preferably used. There is also no particular limitation to the drying temperature, but the temperature range is preferable between 35° C. and 60° C. If necessary, drying under ventilation is preferably conducted. To prevent unwanted decomposition by light, drying in the dark is preferable.

(2) Step of grinding the fruit body dried in Step (1) to prepare a dried/ground sample. This can enhance the efficiency of extraction as described below. There is also no particular limitation to the grinding method, and polishing or grinding can be done with a polisher or grinder either of which is ordinarily used.

(3) Step of extracting the dried/ground sample that is obtained in Step (2) with a solvent. This allows a crude extract to be yielded after removal of the solvent. The extraction solvent that can be used in this invention may be either of a water-miscible solvent and a water-immiscible solvent. For the water-miscible solvent, there may specifically be mentioned methanol and any other lower alcohols either of which may be used alone or in combination with buffer or water. For the water-immiscible solvent, there may specifically be mentioned diethyl ether, ethyl acetate, chloroform, dichloromethane, etc. Especially, extraction with methanol or with ethyl acetate is preferred, because it gives the highest recovery rate and extraction efficiency.

(4) Step of carrying out concentration by removal of the extraction solvent to prepare a crude extract. There is no particular limitation to said method, and for example, the solvent can be removed under reduced pressure. Further, if necessary, it is possible to dry the crude extract. under reduced pressure.

(5) Step of performing silica-gel chromatography to separate a component having a tumor cell proliferation inhibitory activity from the crude extract obtained in Step (4). This allows an eluted fraction containing said component to be yielded. It is preferred that this step be repeated twice or more if required. Here, by measuring the activity of each of the successively eluted fractions, it is possible to determine the active fraction having antitumor activity.

Any known column materials with a variety of properties can be used for chromatography, but silica gel chromatography is preferably used in this invention. It is easy for one skilled in the art to appropriately select conditions such as the kind of usable silica gel, particle size, packing quantity, and the length of the column in view of the quantity of the crude extract, the quantity of impurities, the desirable degree of separation (purity), and the like. Furthermore, by repeating silica gel chromatography twice or more, active fractions with higher purity may be obtained.

There is no particular limitation to the eluting solvent for use in the first silica-gel chromatography. Nonpolar solvents, combinations of nonpolar solvents with polar solvents, and polar solvents alone or in combination may be used. In this invention, the use of a solvent mixture such as n-hexane-ethyl acetate or ethyl acetate-methanol is particularly preferable. It is easy for one skilled in the art to appropriately adjust the mixing ratios of these solvent mixtures for use. There is also no particular limitation to the number of eluted fractions. Separation may be carried out to such extent that will allow any change in the activity of each eluted fraction to be distinguished from each other: on the order of five fractions, as specifically shown in FIG. 1B for Example 1. Fractions with the greatest activity (the activity having a proliferation inhibitory activity specific to tumor cells) may be obtained: for example, F4 shown in FIG. 1B for Example 1.

To obtain active fractions with higher purity, or to isolate active components, the aforementioned fraction(s) can be again subjected to silica gel column chromatography. In this case, the eluent should preferably be more nonpolar. For example, if a mixture of dichloromethane and methanol is employed and the mixing ratio of solvents is gradually adjusted, it is possible to obtain an active fraction with higher purity: C5 as specifically shown in FIG. 1B for Example 1. There is also no particular limitation to the number of eluted fractions. Separation may be carried out to such extent that will allow any change in the activity of each eluted fraction to be distinguished from each other: on the order of 10 fractions, as specifically shown in FIG. 1B for Example 1.

Figure 2:
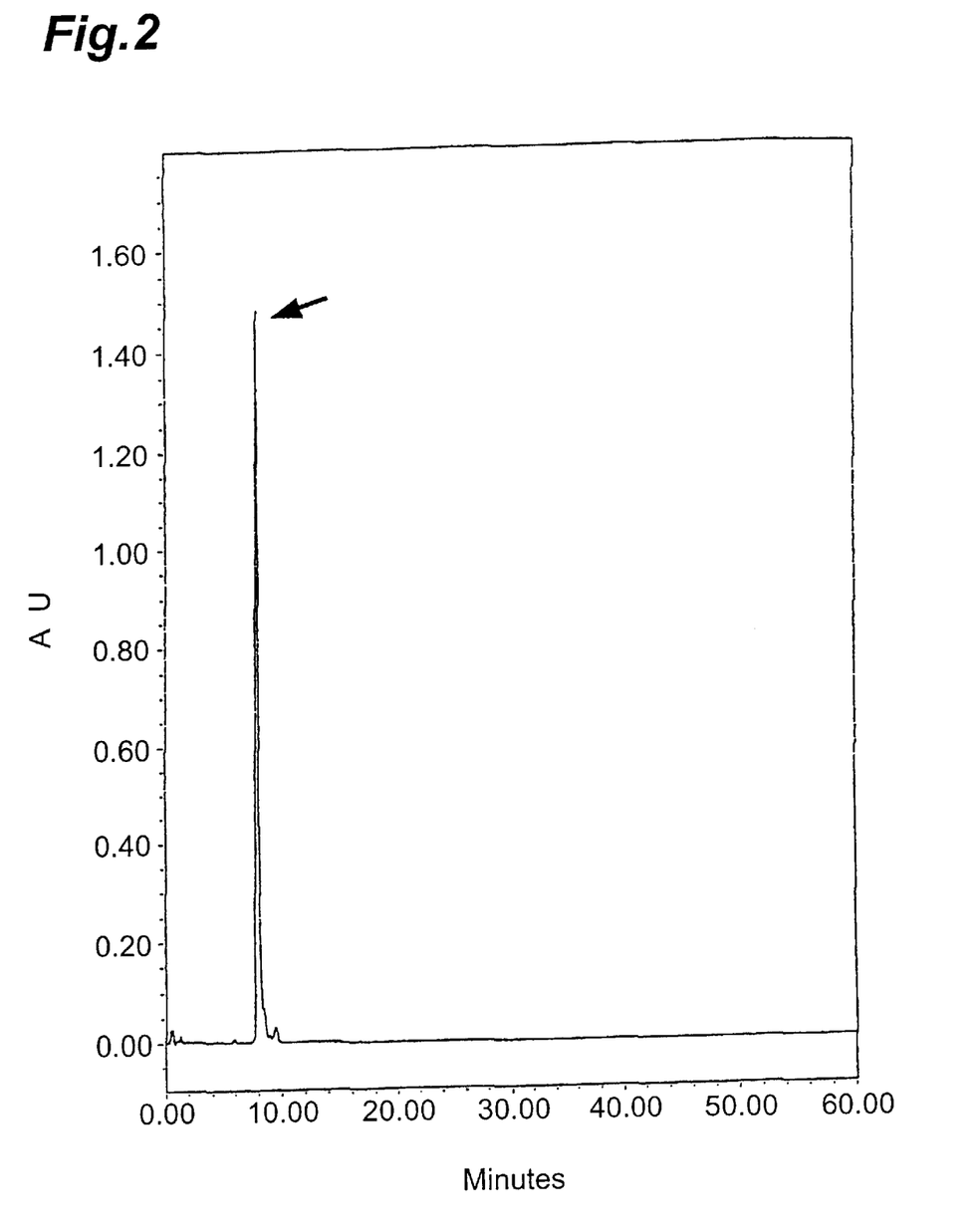
FIG. 2 is a graph showing a reverse phase high performance chromatogram of compound (II) separated and purified according to the invention as obtained in Example 1. Arrow indicates the peak of compound (II). Here, retention time was measured from the sample injection time having been set at 0 min.

(6) Step of separating the active component from the active fraction obtained in Step (5) by chromatography. This allows the separation of compound (1) which is the active component having the antitumor activity contained in Tochukaso. For this purpose, a variety of chromatographic methods with high resolution can be used. Particularly, the-use of thin layer chromatography (referred to as "TLC" hereafter) and/or high performance liquid chromatography (referred to as "HPLC" hereafter) is preferred. The carrier for these kinds of chromatography may be either normal phase or reverse phase, although the reverse phase is particularly preferred. Such chromatographic treatment allows further purification to proceed, whereby there can be obtained an active component that has completely been purified and shows a single peak on HPLC (FIG. 2). Under these conditions, the peak positions on HPLC (e.g., retention times) or the spot positions on TLC (e.g., Rf values) may be utilized in the identification and confirmation of compound (I) of this invention. According to ordinarily known methods, one skilled in the art may readily select conditions such as the kind of TLC carrier, developing solvent, the kind of HPLC carrier, the length of column, the kind of eluent therefor, and the flow rate of solvent.

Using the method of this invention, it is possible to obtain compound (I) in an amount of from 10 mg to 100 mg per 100 g of the fruit body of Tochukaso. It is also possible to obtain even greater quantities or higher yields by altering the extraction method if required.

B. As explained above, the method of this invention purifies compound (I) which is the antitumor component contained in Tochukaso, in accordance with the invention. The general chemical structure of compound (I) indicates a substance having a steroid-like structure represented by the following formula (I) as determined from the results of various physicochemical measurements (based on properties, various chemical characteristic tests, elemental analysis, molecular weight measurement, infrared absorption spectroscopy, ultraviolet absorption spectroscopy, nuclear magnetic resonance spectroscopy and other methods for analysis of chemical structures).

Here, R is generally an acyl group represented by —CO(CH$_2$)$_n$CH$_3$ (n is an integer of from 0 to 5). More specifically, R is an acetyl, propionyl, butyryl, valeryl, hexanoyl, or heptanoyl group. What was separated in Example 1 is a compound having an acetyl group with n being 0 (Formula (II)). Such a structure reveals that it is a compound resembling a totally novel steroidal skeleton which has been hitherto unknown. In addition, said compound contains isomers, including geometric isomers and optical isomers.

These compounds can be obtained following the method according to this invention as explained above, but not limited thereto. Based on the structural formulae, methodologies of chemical synthesis for steroid analogs that are known in the art may be utilized; this readily allows a synthetic pathway to be designed and the synthesis to be made relying thereon.

C. The antitumor agents of this invention are characterized in that they contain active fractions or active components, any of which has the antitumor activity,. contained in Tochukaso that have been explained in A and B above. Specifically, compound (I) obtained by the above-mentioned method has a distinct proliferation inhibitory effect specific to tumor cells. The mechanism of action suggests that compound (I) directly or indirectly cleaves the DNA of tumor cells. That is, compound (I) exhibits no proliferation inhibitory activity against normal cells; despite that, the compound can be used as an antitumor agent since it has a proliferation inhibitory effect specific to tumor cells.

When compound (I) is used as a medicinal preparation, it can be used alone or in combination with known therapeutic agents such as anticancer agents or steroids; and it can be used as such or can be used, together with known excipients, in a suitable dosage form such as a tablet, capsule, injectable, suppository, ointment, cream, gel, lotion, aerosol, buccal, plaster, fomentation, and ophthalmic solution.

Systemic or local administration may be normally done orally or parenterally. The dosage is appropriately determined according to the severity, the age and the sex of the subject, or the like. However, when compound (I) is normally administered an adult, it will be administered in a dose of from about 10 to about 500 mg once to a few times daily.

The examples of this invention are illustrated below; however, the invention is in no way limited by the description of the following examples.

EXAMPLE 1

Extraction of Antitumor Component

Figure 1B:
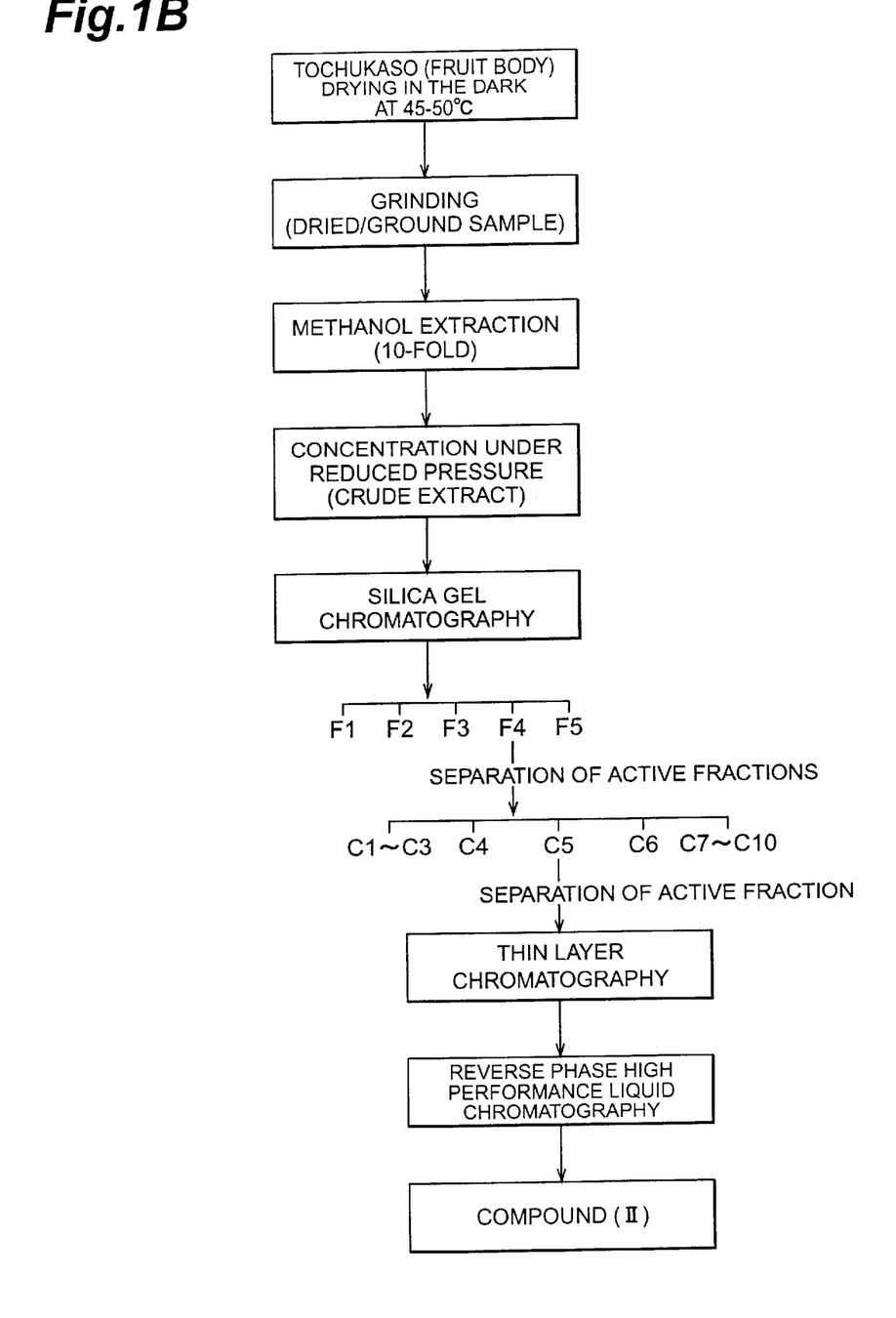
FIG. 1B is a flow chart of extraction of the active fractions and the active component from Tochukaso according to the invention, which was used in Example 1.

Extraction was carried out according to the flow chart in FIG. 1B. The fruit body of Tochukaso (100 g) was dried under heating in a drying box in the dark at 45–50° C. After grinding with a grinder, the fruit body was immersed in 10×methanol (w/v) for 24 h and the extracted solution was concentrated under reduced pressure. Subsequently, the crude extract was subjected to silica-gel column chromatography at the first stage (35×300 mm, Silica-gel 60, 63–100 μm, Merck AG). Solvent of which the polarity was gradually increased (in the order of n-hexane, n-hexane/ethyl acetate (1:1), ethyl acetate, ethyl acetate/methanol (1:1), and methanol) was used, separating a portion eluted with the 1:1 ethyl acetate/methanol (F4 fraction).

Next, F4 fraction was subjected to silica-gel column chromatography at the second stage (35×300 mm, Silica-gel 60, 63–100 μm, Merck AG). A mixture of dichloromethane and methanol was used as an eluting solvent and an eluted portion (C5 was obtained by gradually increasing the mixing ratio of methanol. To further obtain an active component, n-hexane/ethyl acetate (1:1 v/v) was used as a developing solvent in silica-gel thin layer chromatography (TLC Plate Silica-gel 60, F254, Merck AG). TLC was carried out twice to remove the impurities of C5 fraction, and substances whose RF value was in the range of 0.5–0.7 was collected.

Next, reverse phase HPLC was carried out to obtain 50 mg of a completely purified active component from the collected substances. The conditions for HPLC were as follows: eluting solvent: dichloromethane containing 1% (v/v) methanol; column-immobilized phase: silica column (3.9×150 mm, Nova-Pak C18, Nova Biochemicals); the flow rate of eluting solvent: 1 ml/min; and the wavelength of UV spectromeasuring device set to be 254 nm. FIG. 2 shows the results of the completely purified compound as analyzed by the reverse phase chromatography, giving a single peak under the conditions employed. Further, the resulting active component compound satisfy the following physicochemical properties.

Figure 3:
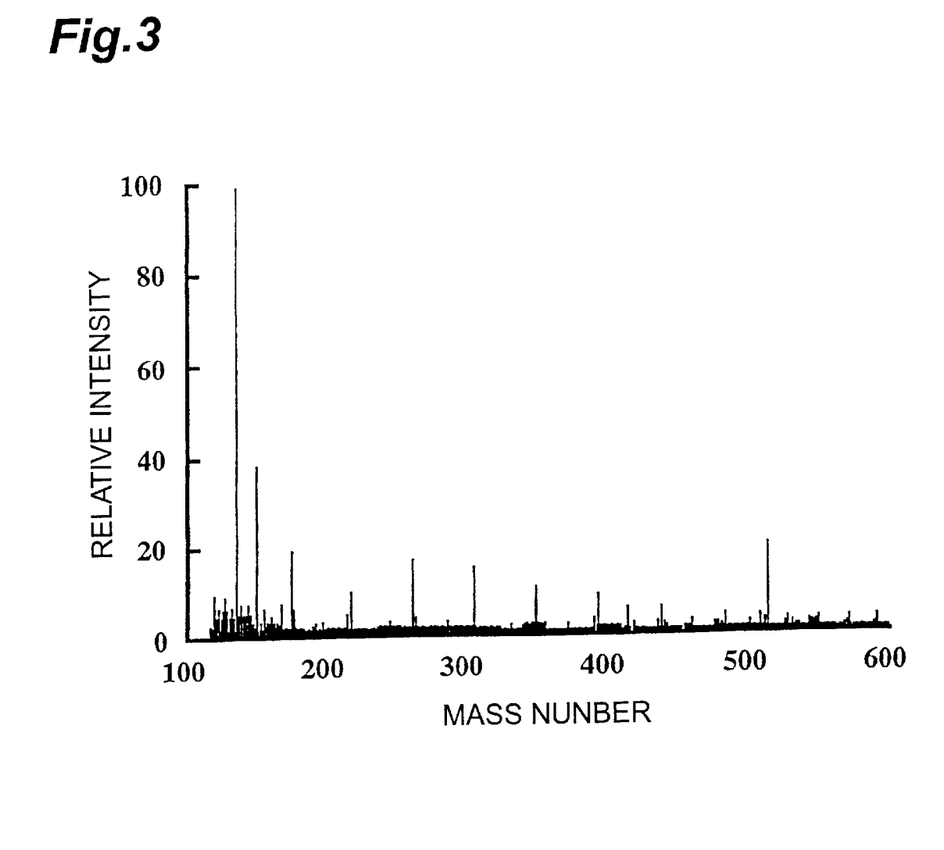
FIG. 3 is a graph showing mass spectral data for compound (II) that is the active component of the invention as obtained in Example 1.

(1) Properties: brown and oily at room temperature;
(2) Molecular formula: $C_{31}H_{58}O_6$;
(3) Mass fragments (FAB)(m/z): 512 (base peak and the same onwards), 482, 437, 393, 349, 305, 261, 217, 175, 149, and 133 (FIG. 3);
(4) IR absorption spectrum $(cm^{-1})$: 3300 (OH), 1725 (C=O), 1645 (C=C), 1430 $(CH_3)$, 1370 $(CH_3CO)$, 1172 (C—CO), and 1138 (C—O); and
(5) UV absorption spectrum (λmax; nm): 225.

From these results, the structural formula for the resulting compound is represented by the following formula (II):

(II)

Test Example 1

In order to demonstrate that the active fraction extracted from Tochukaso containing the active compound exhibits an inhibitory activity specific to the proliferation of tumor cells, an investigation on the proliferation inhibitory activity was carried out using Vero and HeLa cells. Here, Vero was a tumor cell line derived from the kidney of a grivet, and HeLa was a tumor cell line derived from human cervix.

These cells were grown in FCS-MRM medium. The respective cells were trypsinized and washed with a FCS-free RPMI culture medium three times. The cell density was adjusted to 50,000 cells/ml prior to the test. Each 200 μl of cell suspension was dropped into a 96-well plain-bottom plate.

After one day, the culture medium was aspirated; and 200 μl of an active component solution was dropped into test wells, and 200 μl of DMSO dropped into control wells. The plate was incubated in a 5% $CO_2$ atmosphere at 37° C. for 3 days. Ten μl of Alarmer Blue (staining agent) was added to each well, and incubation continued for additional 3 hrs. The tumor cell proliferation inhibitory activity was determined spectrophotometrically (570 and 600 nm) according to the following equation:

Eq. Proliferation inhibitory activity=100%−[(absorbance of test well)/(absorbance of control well)×100%]

Figure 5:
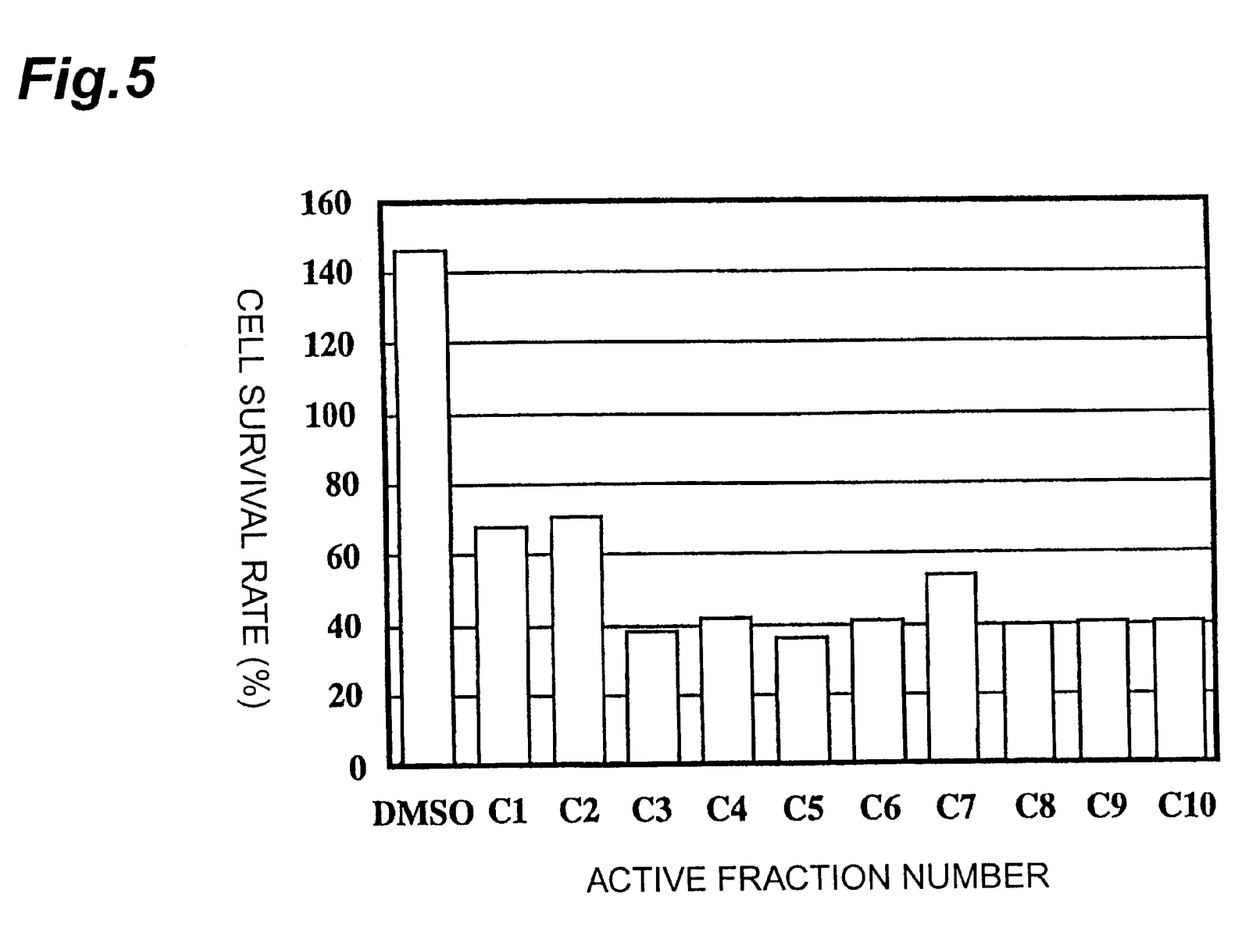
FIG. 5 is a graph showing the cell proliferation inhibitory activity of different fractions that were separated/extracted according to this invention (fractions C1–C10 in FIG. 1B) against Vero cells.
Figure 6:
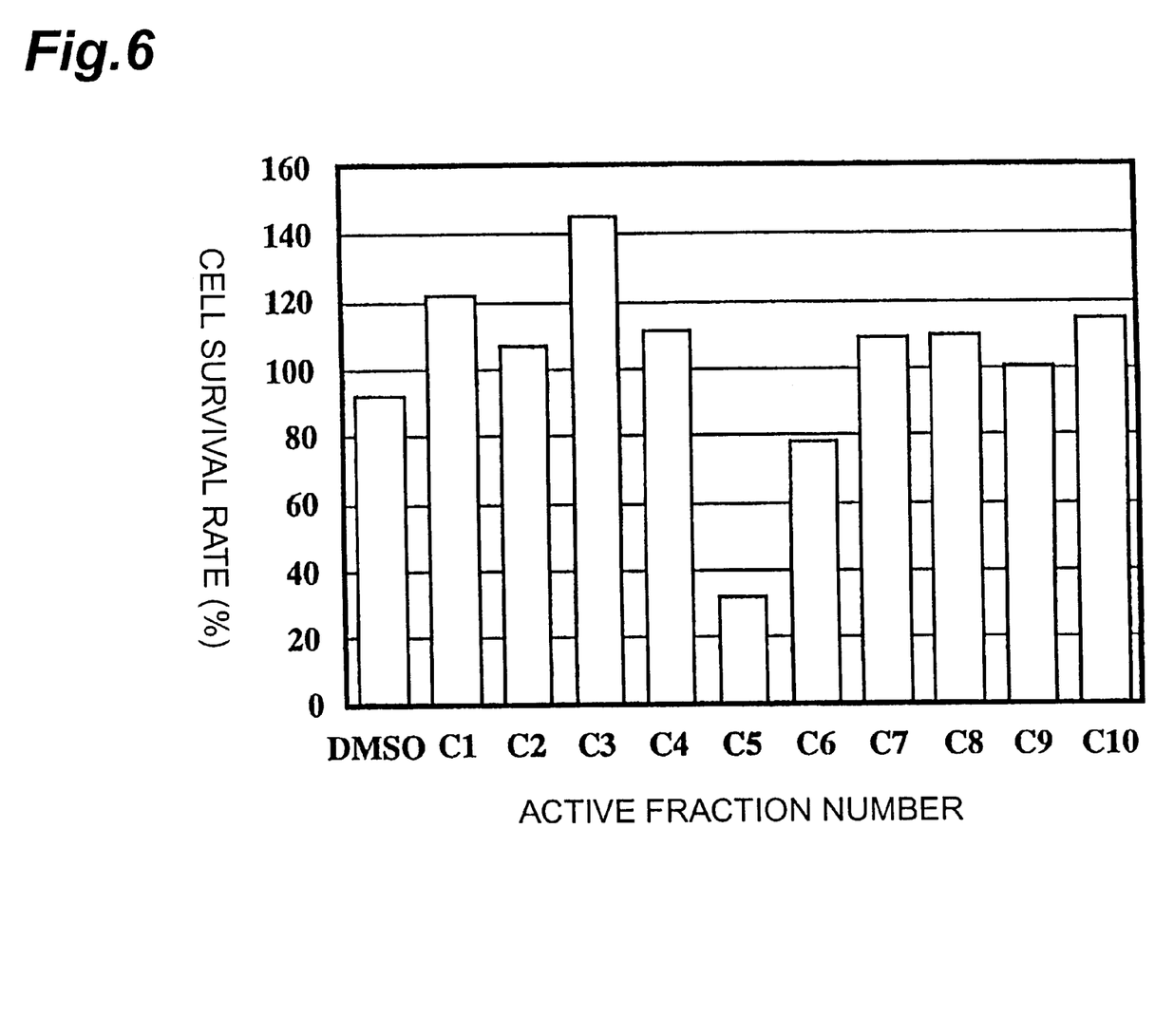
FIG. 6 is a graph showing the cell proliferation inhibitory activity of the different fractions that were separated/extracted according to this invention (fractions C1–C10 in FIG. 1B) against HeLa cells.

A similar experiment was also carried out for evaluation in fibroblasts. Results are shown in FIGS. 4–6.

Figure 4:
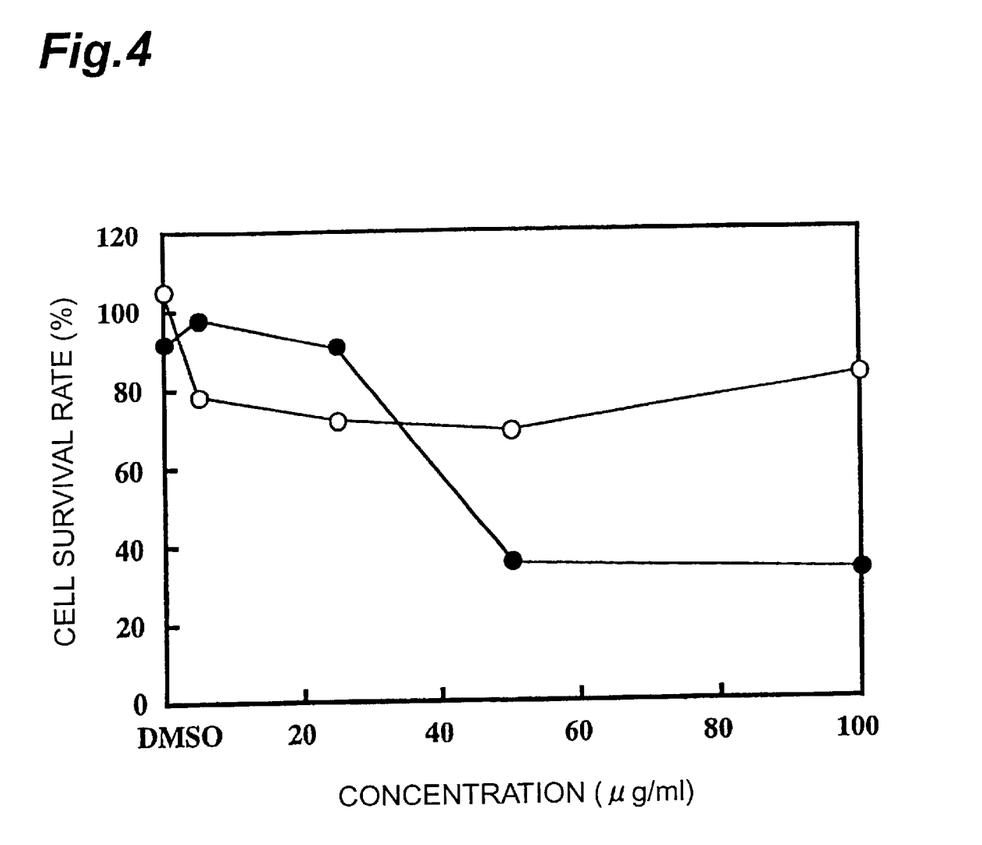
FIG. 4 is a graph showing the cell proliferation inhibitory activity (dose-dependency) of the active component of this invention (C5 fraction in FIG. 1B). Here, "○" and "●" represent the results with fibroblasts and those with HeLa cells, respectively.

FIG. 4 shows the concentration-dependence of the tumor cell proliferation inhibitory activity for active fraction C5, where the inhibitory activity was observed in a dose-dependent manner for both cells. FIG. 5 shows the proliferation inhibitory activity of each of fractions C1–C5 (plus DMSO addition as a control) against the Vero cells (expressed as cell survival rate), where all the fractions posses a recognizable, remarkable inhibitory activity as compared to the control. FIG. 6 shows the proliferation inhibitory activity of each of fractions C1–C5 (plus DMSO addition as a control) against the HeLa cells (expressed as cell survival rate), where particularly, the C5 fraction possesses a recognizable, very remarkable inhibitory activity as compared to the control.

From these results, it has become apparent that the active fraction and the active component of this invention exhibit a remarkable proliferation inhibitory activity specific to tumor cells.

Test Example 2

In order to demonstrate that the active fraction extracted from Tochukaso possesses antitumor activity by displaying a cleavage action specific to the tumor cell DNA, the DNA cleavage was examined against HeLa cells. HeLa cells were prepared, adjusted to a cell density of $1×10^6$ cells/ml in a φ10 cm culture dish and grown, into which 200 μl of the active fraction solution was dropped. Cells were harvested each 50 μl after 24, 48, and 72 hrs, and incubated in 400 μl of culture solution (containing Tris-EDTA, SDS and Proteinase K) in a 5% $CO_2$ atmosphere at 37° C. overnight. NaCl was added to the cells and decomposed proteins were centrifuged; and the supernatant was precipitated in ethanol.

Figure 7:
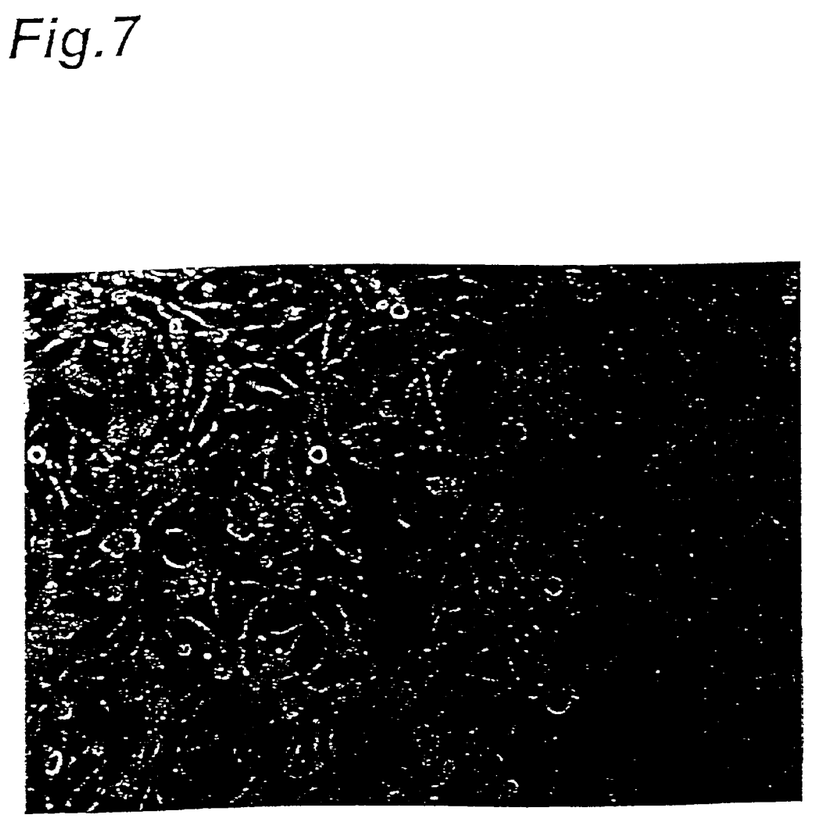
FIG. 7 is a photograph showing chromatin aggregation within a HeLa cell (24 hours) resulting from DNA fragmentation.
Figure 8:
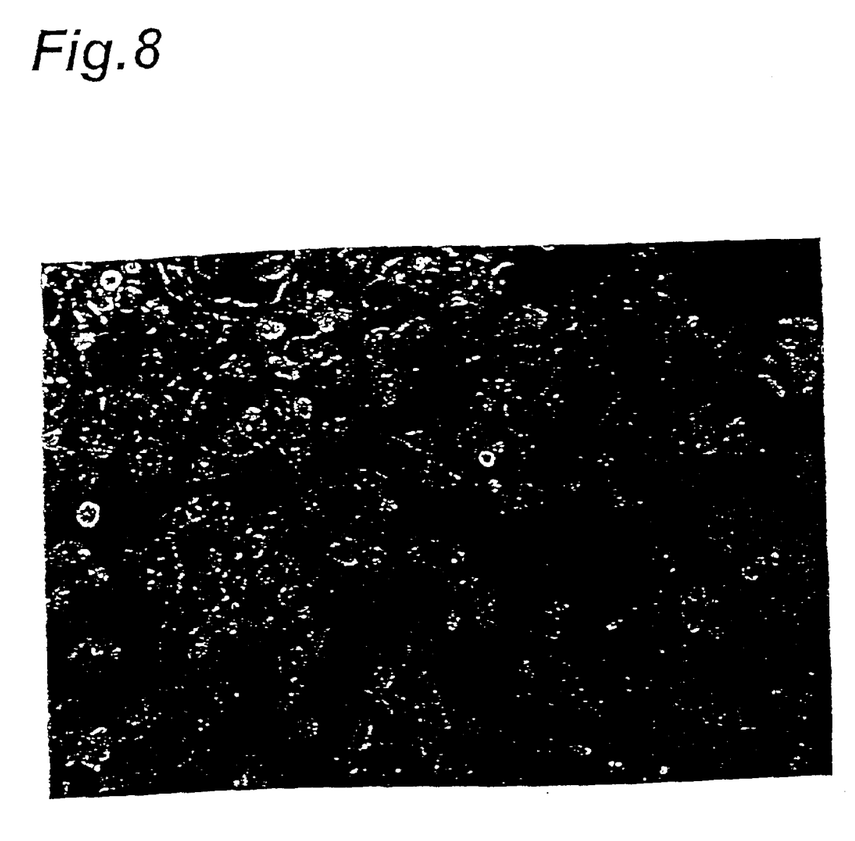
FIG. 8 is a photograph showing chromatin aggregation within a HeLa cell (72 hours) resulting from DNA fragmentation.
Figure 9:
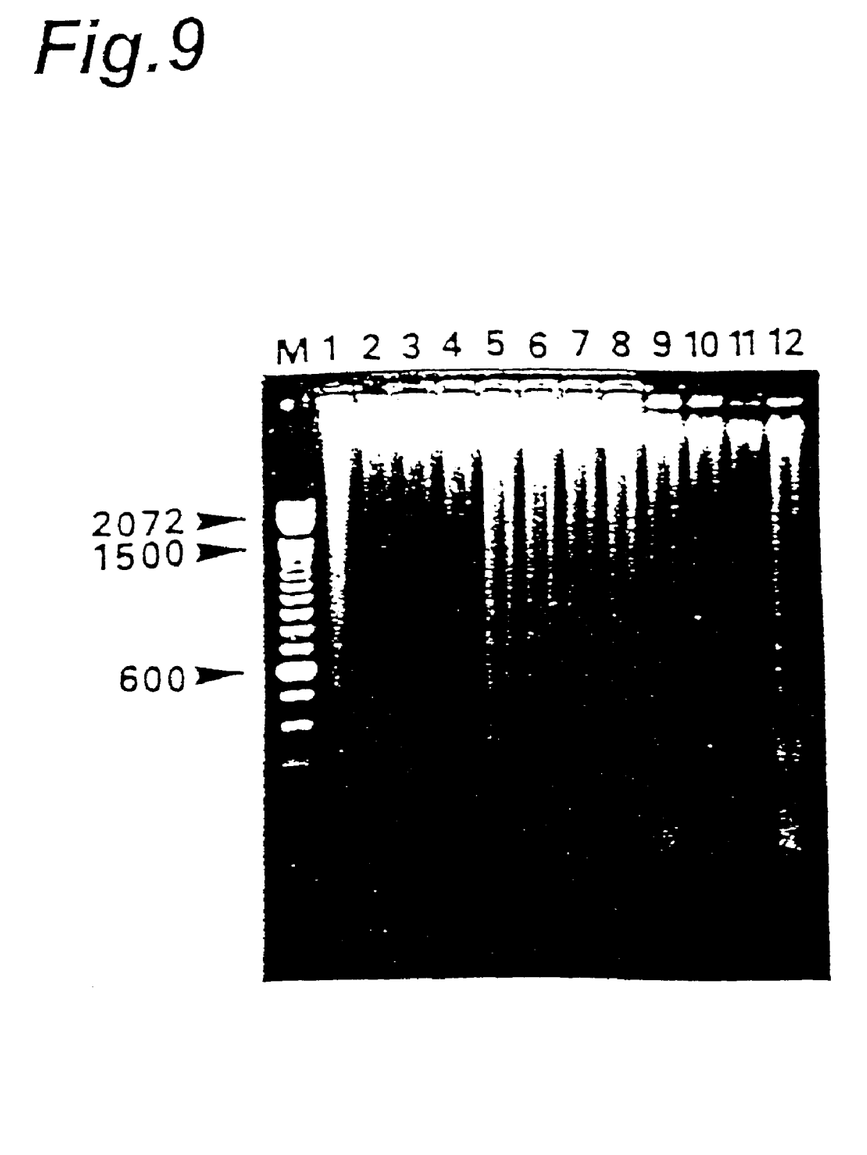
FIG. 9 is a photograph showing the results of electrophoresis of cellular HeLa DNA. Here, Lanes 1–4 represent the results after 24 hours, Lanes 5–8 the results after 48 hours, and Lanes 9–12 the results after 72 hours. "M" and numerals indicate molecular markers and molecular weights therefor.

The precipitate was suspended in Tris-EDTA buffer containing RnaseA. After 2 hrs, it was loaded onto agarose gel. After staining with ethidium bromide, it was electrophoresed and visualized under UV irradiation. As FIGS. 7 and 8 show the results, chromatin aggregation was observed in the cell nuclei. As FIG. 9 also shows, the result of electrophoresis indicates that the DNAs have shifted to low molecular weight ranges. These results revealed that the active compound induces apotosis in the tumor cells.

INDUSTRIAL APPLICABILITY

This invention enables the separation of antitumor fractions or components contained in Tochukaso. Further, it reveals the chemical structure of the component having the activity. Still further, there are provided an antitumor agent containing the antitumor fraction or component contained in Tochukaso.

What is claimed is:
1. A method for separating an active fraction and an active component from Tochukaso, said active fraction and said active component having antitumor activity, said method comprising:
   drying a fruit body of Tochukaso;
   grinding said dried fruit body to prepare a dried ground sample;
   extracting said sample with a water-miscible solvent to prepare an extracted solution;
   concentrating said extracted solution to prepare a crude extract;

separating said crude extract at least once by silica gel column chromatography to obtain an eluted fraction having tumor cell proliferation inhibitory activity and to prepare the active fraction; and purifying said active fraction using chromatographic separation comprising thin layer chromatography or high performance liquid chromatography to separate the active component having tumor cell proliferation inhibitory activity, wherein the active component is a compound represented by formula (I):

(I)

wherein said formula R is an acyl group represented by the formula —$CO(CH_2)_nCH_3$ in which n is an integer from 0 to 5.

2. The method according to claim 2, wherein said active component is a compound presented by formula (II):

(II)

said compound:
(a) being brown and oily at room temperature;
(b) having a molecular formula $C_{31}H_{58}O_6$;
(c) having major mass fraction peaks (FAB)(m/z) of 512 (base a), 482, 437, 393, 349, 305, 261, 217, 175, 149, and 133;

(d) having an IR absorption spectrum (cm −1) of: 3300, 1725, 1645, 1430, 1376, 1172, and 1138; and
(e) having an UV absorption spectrum (λ max; nm) of 225.

3. An antitumor agent comprising a compound represented by the formula (I):

(I)

wherein R is an acyl group represented by the formula —$CO(CH_2)_nCH_3$ in which n is an integer of o to 5.

4. The antitumor agent according to claim 3, wherein said compound is represented by the formula:

(II)

said compound:
(a) being brown and oily at room temperature;
(b) having a molecular formula $C_{31}H_{58}O_6$;
(c) having major mass fraction peaks (FAB)(m/z) of 512 (base peak), 482, 437, 393, 349, 305, 261, 217, 175, 149, and 133;
(d) having an IR absorption spectrum (cm −1) of: 3300, 1725, 1645, 1430, 1370, 1172, and 1138; and
(e) having an UV absorption spectrum (λ max; nm) of 225.

* * * * *